(12) United States Patent
Sun et al.

(10) Patent No.: US 11,840,502 B2
(45) Date of Patent: Dec. 12, 2023

(54) SYSTEM AND METHOD FOR EFFICIENTLY PREPARING TAURINE

(71) Applicant: HUBEI GRAND LIFE SCIENCE AND TECHNOLOGY CO., LTD., Hubei (CN)

(72) Inventors: Huajun Sun, Hubei (CN); Min Tan, Hubei (CN); Xiaojing Yan, Hubei (CN); Ruyong Jiang, Hubei (CN); Hongbo Peng, Hubei (CN); Jiale Tang, Hubei (CN); Chen Guo, Hubei (CN); Xingxing Wang, Hubei (CN); Zhiqiang Qian, Hubei (CN)

(73) Assignee: HUBEI GRAND LIFE SCIENCE AND TECHNOLOGY CO., LTD., Hubei (CN)

( * ) Notice: Subject to any disclaimer, the term of this patent is extended or adjusted under 35 U.S.C. 154(b) by 3 days.

(21) Appl. No.: 17/808,925

(22) Filed: Jun. 24, 2022

(65) Prior Publication Data

US 2022/0324793 A1  Oct. 13, 2022

Related U.S. Application Data

(63) Continuation of application No. PCT/CN2021/107399, filed on Jul. 20, 2021.

(30) Foreign Application Priority Data

Mar. 25, 2021  (CN) .......................... 202110322108.2

(51) Int. Cl.
*B01D 15/36* (2006.01)
*C07C 303/22* (2006.01)
*C07C 303/44* (2006.01)

(52) U.S. Cl.
CPC .......... *C07C 303/22* (2013.01); *B01D 15/363* (2013.01); *C07C 303/44* (2013.01)

(58) Field of Classification Search
CPC .... C07C 303/22; C07C 303/44; B01D 15/363
See application file for complete search history.

(56) References Cited

U.S. PATENT DOCUMENTS

| 2,693,488 A | 11/1954 | Sexton | |
| 9,061,976 B1* | 6/2015 | Hu | ......................... C07C 303/44 |
| 2010/0144908 A1* | 6/2010 | Campbell | ................ B01J 49/53 |
| | | | 521/26 |

FOREIGN PATENT DOCUMENTS

| CN | 107056659 A | 8/2017 |
| CN | 110452136 A | 11/2019 |

(Continued)

OTHER PUBLICATIONS

Machine translation of CN-210736624.*

(Continued)

*Primary Examiner* — Benjamin L Lebron
(74) *Attorney, Agent, or Firm* — Lee & Hayes, P.C.

(57) ABSTRACT

The present disclosure provides a system for efficiently preparing taurine, including: a solution storage unit configured to store a solution containing alkali metal taurinate, the solution being prepared by an ethylene oxide process; an ion exchange unit including at least one ion exchange resin column each configured to be activated by a first activation manner or a second activation manner independently, the first activation manner using sulfurous acid for activation to obtain alkali metal bisulfate and taurine, and the second activation manner using sulfuric acid for activation to obtain alkali metal sulfate and taurine; and a dispensing unit connected to the solution storage unit and the ion exchange unit respectively, and configured to adjust an amount of a (Continued)

solution conveyed from the solution storage unit to each of the at least one ion exchange resin column in the ion exchange unit.

20 Claims, 4 Drawing Sheets

(56) References Cited

FOREIGN PATENT DOCUMENTS

| CN | 111039832 | A |   | 4/2020 | | |
|----|-----------|---|---|--------|---|---|
| CN | 210736624 | U | * | 6/2020 | ……… | C07C 303/06 |
| CN | 111471002 | A |   | 7/2020 | | |
| CN | 111592473 | A |   | 8/2020 | | |
| CN | 113072468 | A |   | 7/2021 | | |
| JP | 2003221370 | A |   | 8/2003 | | |
| JP | 2019001772 | A |   | 1/2019 | | |
| JP | 2019128091 | A | * | 8/2019 | ……… | B01D 53/002 |
| JP | 2021038216 | A |   | 3/2021 | | |

OTHER PUBLICATIONS

Machine translation of JP-2019128091.*
Chinese Office Action dated Jan. 5, 2022 in Chinese Application No. 202110322108.2, 7 pages. Translated.
Chinese Search Report dated Dec. 28, 2021 in Chinese Application No. 202110322108.2, 1 page.
International Search Report and Written Opinion dated Dec. 9, 2021 in International Application No. PCT/CN2021/107399, 4 pages.
Japanese Office Action dated Mar. 22, 2023 in Japanese Application No. 2022-541646, a corresponding foreign application of U.S. Appl. No. 17/808,925, 8 pages.

* cited by examiner

SYSTEM AND METHOD FOR EFFICIENTLY PREPARING TAURINE

CROSS-REFERENCE TO RELATED APPLICATIONS

The present application is a continuation of International application No. PCT/CN2021/107399, filed on Jul. 20, 2021, which claims priority to and benefits of Chinese Patent Application No. 202110322108.2 filed before the China National Intellectual Property Administration on Mar. 25, 2021, the entire contents of which are incorporated herein by reference.

TECHNICAL FIELD

The present disclosure relates to the field of chemical engineering, and specifically relates to a system and method for efficiently preparing taurine.

BACKGROUND

Taurine is a special sulfur-containing amino acid, which has anti-inflammatory, antipyretic, analgesic, anticonvulsant, and blood pressure-lowering effects as a drug. As a health product, it also has good promotion effects on brain development, nerve conduction, improvement of visual function, and calcium absorption of infants and children.

China, as the world's largest taurine production base, contributes about 5 tons of taurine raw materials prepared by an ethylene oxide process annually. The ethylene oxide process for preparing taurine includes the following three steps.

(1) Addition reaction

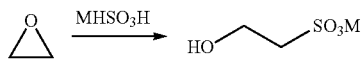

Ethylene oxide is reacted with alkali metal bisulfate to prepare alkali metal isethionate.

(2) Ammonolysis reaction

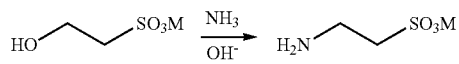

The alkali metal isethionate is reacted with ammonia under alkaline conditions to prepare an alkali metal taurinate. In the reaction process, excessive ammonia is required. Therefore, redundant ammonia needs to be removed by a flash vaporization and evaporation step after the reaction is completed, and the solution obtained after evaporation is called as evaporated solution.

(3) Neutralization reaction

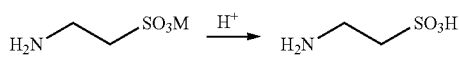

Alkali metal ions in the alkali metal taurinate are replaced with hydrogen ions under acidic conditions so as to prepare taurine.

However, the existing production process of taurine is complicated and inefficient. Especially, in the continuous production process, a large number of intermediate products will be produced, and a lot of water will be consumed, causing the waste of resources. Therefore, there is a need for developing a novel taurine preparation method.

SUMMARY

Commonly used methods for acidizing alkali metal taurinate include a sulfuric acid neutralization method, which produces sulfate, an electrolytic method and an ion exchange method, which do not produce sulfate, etc. Although the ion exchange method, which does not produce sulfate, is provided in the related art, the inventors have found that the method wastes a lot of water and other resources because the ion exchange process requires many tedious steps such as washing ion exchange columns with water, and diluting materials before the materials are input into the ion exchange columns. In addition, alkali metal bisulfite as a byproduct produced in the ion exchange process will be further recycled and reused in the hydroxylation process. However, in the continuous production process, an intermediate material is input into an ion exchange system directly without being separated. Therefore, alkali metal ions in alkali metal taurinate are transformed into alkali metal bisulfite by an ion resin, and alkali metal ions contained in the alkali for providing an alkaline environment in the ammonolysis reaction process are also transformed into alkali metal bisulfite. As one molecule of ethylene oxide only consumes one molecule of alkali metal bisulfite, alkali metal ions in the whole system are unbalanced. In order to achieve the balance of alkali metal ions, theoretically a part of an alkali metal bisulfite solution can be collected and sold. However, the alkali metal bisulfite solution outputted from the ion exchange system contains some impurities and does not have a quality required for selling. Therefore, in order to solve the above problem, the present disclosure provides an efficient taurine preparation system and method.

In a first aspect, the present disclosure proposes a system for efficiently preparing taurine. According to embodiments of the present disclosure, the system includes: a solution storage unit configured to store a solution containing alkali metal taurinate, the solution being prepared by an ethylene oxide process; an ion exchange unit including at least one ion exchange resin column each configured to be activated independently by a first activation manner or a second activation manner, the first activation manner using sulfurous acid for activation to obtain alkali metal bisulfite and taurine, and the second activation manner using sulfuric acid for activation to obtain alkali metal sulfate and taurine; and a dispensing unit connected to the solution storage unit and the ion exchange unit, the dispensing unit being configured to adjust an amount of the solution conveyed from the solution storage unit to each of the at least one ion exchange resin column in the ion exchange unit. The system according to the embodiments of the present disclosure can control the balance of alkali metal ions in the system in a continuous production process of taurine. Reaction materials including ethylene oxide and alkali metal bisulfite react to produce alkali metal taurinate, the obtained alkali metal taurinate can be acidized into taurine in the ion exchange unit, the ion exchange resin columns in the ion exchange unit can be activated by multiple activation manners, the first activation manner uses sulfurous acid for activation so as to obtain alkali metal bisulfite and taurine, and the second activation manner uses sulfuric acid for activation so as to obtain alkali metal sulfate and taurine. In addition, in order to increase the acidity of a sulfurous acid solution serving as an activating reagent, the sulfurous acid solution also contains alkali metal bisulfite. It can be known from the chemical formulas, alkali metal bisulfite corresponds to finally produced taurine in a ratio of 1:1. Moreover, at the neutralization reaction step, the produced taurine corresponds to the produced alkali metal ions in a ratio of 1:1. When the ion exchange unit is activated by the first activation manner, the first activating reagent contains alkali metal bisulfite, and alkali metal ions in alkali metal taurinate will be also transformed into alkali metal bisulfite in the activation process. In addition, an ammonolysis reaction needs to be performed under alkaline conditions, so that residual alkali metal ions in the system will be also transformed into alkali metal bisulfite after the ammonolysis reaction is completed. Therefore, excessive alkali metal bisulfite will be produced. By introducing the second activation manner using sulfuric acid as an activating reagent, the excessive alkali metal ions produced by the first activation manner can be depleted, and thus the excessive alkali metal ions are concentrated and collected as alkali metal sulfate finally to achieve the balance of the alkali metal ions. The system according to the embodiments of the present disclosure is well designed and suitable for achieving the balance of alkali metal ions in the continuous mass production without requiring for an extra production line for solving the problem of excessive alkali metal ions, and can achieve the balance of alkali metal ions in the production process of taurine, thereby improving the production efficiency of taurine while saving cost.

According to embodiments of the present disclosure, the system can further include at least one of the following additional technical features.

According to the embodiments of the present disclosure, the system further includes an activating solution change unit connected to each of the at least one ion exchange resin column and configured to adjust an activation manner of the ion exchange resin column. The inventors have found that if the ion exchange resin column is continuously activated with an alkali metal bisulfite solution in which sulfur dioxide is dissolved in the continuous taurine production process, the ion exchange resin column will be damaged, and the service life of the ion exchange resin column will be reduced; and if the ion exchange resin column is intermittently activated with sulfuric acid, the service life of the ion exchange resin column can be prolonged, and the production efficiency can be improved. The activating solution change unit is a unit for changing an activation manner performed on an ion exchange resin column. Under the action of the unit, an activation manner performed on an ion exchange resin column can be changed from the sulfurous acid activation manner to the sulfuric acid activation manner, or changed from the sulfuric acid activation manner to the sulfurous acid activation manner.

According to the embodiments of the present disclosure, the system further includes an alkali metal ion concentration detection module connected to an inlet and an outlet of the ion exchange resin column. The alkali metal ion concentration detection module is adapted to independently detect a concentration of alkali metal ions in an input solution of the ion exchange resin column and a concentration of alkali metal ions in an output solution of the ion exchange resin column. Both the input solution and the output solution contain alkali metal taurinate. The alkali metal ion concentration detection module is connected to the activating solution change unit to allow the activating solution change unit to adjust the activation manner of the ion exchange resin column based on a detection result of the alkali metal ion concentration detection module. According to the embodiments of the present disclosure, the alkali metal ion concentration detection module can accurately determine the concentrations of alkali metal ions in an input solution and in an output solution of each ion exchange resin column, and the state of service of each ion exchange resin column is judged according to the comparison results, so as to guide the activating solution change unit to change an activation manner from the sulfurous acid activation manner to the sulfuric acid activation manner, or from the sulfuric acid activation manner to the sulfurous acid activation manner.

According to the embodiments of the present disclosure, the dispensing unit is configured to adjust an amount of the solution conveyed from the solution storage unit to each of the at least one ion exchange resin column independently. The amount of the solution inputted into the at least one ion exchange resin column treated by the first activation manner is 60 wt % to 95 wt % of a total amount of the solution in the solution storage unit. The amount of the solution inputted into the at least one ion exchange resin column treated by the second activation manner is 5 wt % to 40 wt % of the total amount of the solution in the solution storage unit. According to the embodiments of the present disclosure, the amount of the solution inputted into the at least one ion exchange resin column treated by the second activation manner is 5 wt %, 10 wt %, 15 wt %, 20 wt %, 25 wt %, 30 wt %, 35 wt % or 40 wt % of the total amount of the solution in the solution storage unit. Upon extensive studies, the inventors have found that in the production process of taurine with the system of the present disclosure, extra strong alkali is added in the ammonolysis reaction process to adjust a pH value of the reaction system, and a small part of the strong alkali for adjusting the pH value will consume some active groups in a resin in the ion exchange process. If the ion exchange resin column is activated with sulfurous acid, one metal ion is displaced with one sulfurous acid to form an alkali metal salt, and one alkali metal salt can correspondingly produce one taurine molecule. Thus, if the ion exchange resin column is activated with sulfurous acid that is produced by dissolving sulfur dioxide with alkali metal bisulfite, excessive alkali metal bisulfite is present in the production system, a part of the alkali metal bisulfite cannot be recycled and reused, and then excessive alkali metal ions are present in the production system. In order to solve this problem, a redundant alkali metal bisulfite solution needs to be disposed. However, the direct sewage disposal is high in cost and low in efficiency; and if an evaporation and concentration process is adopted, sodium bisulfite, sodium sulfite, etc. are unstable, the resulting salt is unsaleable because of its high levels of impurities, causing the waste of materials. By extensive studies and a large number of experimental designs, the inventors have found that if the ion exchange resin columns activated by the first activation manner and the second activation manner are used to produce taurine from an evaporated solution at the same time, during the activation of the ion exchange resin columns with sulfuric acid, a part of alkali metal ions can be transformed into alkali metal sulfate that belongs to strong alkali salts, and the alkali metal sulfate can be directly concentrated by evaporation to form a pure product that can be sold or used. The disposal method is simple and saves cost and resources.

According to the embodiments of the present disclosure, a ratio of the amount of the solution inputted into the at least one ion exchange resin column treated by the first activation manner to the amount of the solution inputted into the at least one ion exchange resin column treated by the second activation manner ranges from (3:2) to (19:1).

According to the embodiments of the present disclosure, the activating solution change unit is configured to change, in response to the concentration of alkali metal ions in the output solution of the ion exchange resin column that is being treated by the first activation manner being greater than 60% of the concentration of alkali metal ions in the input solution of the ion exchange resin column, the activation manner of the ion exchange resin column to the second activation manner, and change, in response to the concentration of alkali metal ions in the output solution being smaller than or equal to 5% of the concentration of alkali metal ions in the input solution, the activation manner of the ion exchange resin column to the first activation manner. According to the embodiments of the present disclosure, when the concentration of alkali metal ions in the output solution is greater than or equal to 60% of the concentration of alkali metal ions in the input solution, it indicates that the ion exchange resin column is not in a good service condition, because excessive alkali metal ions are present in the ion exchange resin column, ion exchange performed on alkali metal taurinate is inefficient, the activation manner performed on the ion exchange resin column needs to be changed, and the ion exchange resin column needs to be activated with sulfuric acid. When the concentration of alkali metal ions in the output solution is smaller than or equal to 5% of the concentration of alkali metal ions in the input solution, it indicates that the ion exchange resin column is in a recovered state and can be further activated with sulfurous acid (an alkali metal bisulfite solution in which sulfur dioxide is dissolved). The efficiency of activation with sulfurous acid is higher, which is beneficial to the efficient preparation of taurine in the continuous production process.

According to the embodiments of the present disclosure, the system further includes: a solution allocation module connected to a bottom of each of the at least one ion exchange resin column, and configured to input an alkali metal bisulfite solution into the ion exchange resin column from bottom to top before the ion exchange resin column is treated by the first activation manner, and input an alkali metal sulfate solution into the ion exchange resin column from bottom to top before the ion exchange resin column is treated by the second activation manner. Upon extensive studies, the inventors have found that treatment of an ion exchange resin column with an alkali metal salt solution from bottom to top before the ion exchange resin column is activated with a strong acid solution can improve the efficiency of subsequent activation of the ion exchange resin column, and reduce the activation time.

According to the embodiments of the present disclosure, the sulfurous acid used by the first activation manner is obtained by dissolving sulfur dioxide in an alkali metal bisulfite solution having a concentration from 25 wt % to 50 wt %. According to the embodiments of the present disclosure, an activating reagent used by the first activation manner is different from an activating reagent used by the second activation manner. The first activation manner mainly uses sulfurous acid for activation. Sulfur dioxide is dissolved in an alkali metal bisulfite solution to increase the solubility of sulfur dioxide so as to produce the sulfurous acid for activation by the first activation manner. The inventors have found that if the concentration of the alkali metal bisulfite solution is 25 wt % to 50 wt %, the resulting solution has a good activation effect on an ion exchange resin column, the activation time is short, and the efficiency is high.

According to the embodiments of the present disclosure, the second activation manner including activating the ion exchange resin column using sulfuric acid at a concentration smaller than or equal to 25 wt %, preferably smaller than or equal to 23 wt %. According to the embodiments of the present disclosure, efficient activation of the ion exchange resin column can be achieved by the second activation manner using sulfuric acid at a concentration smaller than or equal to 25 wt %. Upon extensive studies, the inventors have found that in the continuous production process of taurine, if an ion exchange resin column is continuously activated with an alkali metal bisulfite solution in which sulfur dioxide is dissolved, the ion exchange resin column will be damaged, causing reduction of the exchange efficiency of the ion exchange resin column, shortening the service life, increasing the production cost, etc. However, compared with activation with sulfuric acid only, activation of the ion exchange resin column with sulfurous acid has a lower cost. Thus, in the continuous production process of taurine, the ion exchange resin column can be mainly activated with sulfurous acid, and changed to be activated with sulfuric acid according to the condition of the ion exchange resin column, which can efficiently improve the exchange efficiency, prolong the service life of the ion exchange resin column, improve the production efficiency, and reduce the production cost.

According to the embodiments of the present disclosure, the system further includes: a reaction unit connected to the solution storage unit and configured to prepare an evaporated solution containing the alkali metal taurinate by the ethylene oxide process; and an alkali metal bisulfite pipeline connected to the ion exchange unit and the reaction unit respectively, and configured to return the alkali metal bisulfite to the reaction unit. Alkali metal bisulfite in the activating reagent and alkali metal bisulfite produced after activation can flow back to the reaction unit via the alkali metal bisulfite pipeline to undergo an addition reaction with ethylene oxide to produce alkali metal isethionate.

In a second aspect, the present disclosure proposes a method for preparing taurine. According to embodiments of the present disclosure, the method includes: preparing an evaporated solution containing alkali metal taurinate by an ethylene oxide process in a reaction unit; independently treating each of at least one ion exchange resin column in an ion exchange unit by a first activation manner or a second activation manner; dispensing a part of the evaporated solution containing the alkali metal taurinate to the at least one ion exchange resin column treated by the first activation manner to obtain alkali metal bisulfite and taurine, and inputting the alkali metal bisulfite into the reaction unit; and dispensing the other part of the evaporated solution containing the alkali metal taurinate to the at least one ion exchange resin column treated by the second activation manner to obtain alkali metal sulfate and taurine. The method according to the embodiments of the present disclosure uses the ethylene oxide process to prepare taurine, and uses two kinds of ion exchange resin column activation systems to achieve the balance of alkali metal ions in the continuous mass production process of taurine, thereby avoiding the problem of difficult disposal of redundant alkali metal ions produced in the ion exchange columns activated with sulfurous acid (an alkali metal bisulfite solution in which sulfur dioxide is dissolved), and achieving the balance of alkali metal ions in the continuous production process.

According to the embodiments of the present disclosure, the above method further includes at least one of the following additional technical features.

According to the embodiments of the present disclosure, the first activation manner further includes: passing alkali metal bisulfite through the ion exchange resin column from bottom to top; dissolving sulfur dioxide in an alkali metal bisulfite solution to obtain a sulfurous acid solution; and passing the sulfurous acid solution through the ion exchange resin column from top to bottom to treat the ion exchange resin column by the first activation manner. According to the embodiments of the present disclosure, if the ion exchange resin column stays in the sulfurous acid environment for a long time, its activation efficiency will be reduced. Dissolution of sulfur dioxide in an alkali metal bisulfite solution can improve the activation efficiency of the ion exchange resin column, and shorten the activation time, but introduces redundant alkali metal ions which need to be further balanced.

According to the embodiments of the present disclosure, the second activation manner further includes: passing an alkali metal sulfate solution through the ion exchange resin column from bottom to top; and passing a sulfuric acid solution having a concentration smaller than or equal to 25 wt % through the ion exchange resin column from top to bottom to treat the ion exchange resin column by the second activation manner. According to the embodiments of the present disclosure, activation of the ion exchange resin column with sulfuric acid at a concentration smaller than or equal to 25 wt % can have a good activation effect and an improved activation efficiency, and balance the alkali metal ions in the production process of taurine so as to finally produce alkali metal sulfate.

Upon extensive studies, the inventors have found that the activation efficiency and production efficiency can be improved by pre-treating the ion exchange resin column with an alkali metal salt solution from bottom to top before activating the ion exchange resin column with an acid solution. A density of the alkali metal salt solution is higher than that of water, and when flowing from bottom to top, the alkali metal salt solution is hardly mixed with water thoroughly, which is beneficial for the alkali metal salt solution to push out residual aqueous solution in the resin. The solution that is pushed out can directly enter an original evaporated solution system. The alkali metal salt solution may be a received solution with a pH value greater than 5 that is obtained from the previous acid activation and contain a small number of hydrogen ions that can be transformed into alkali metal salt after entering the ion exchange resin column, and the alkali metal salt solution can be completely transformed into alkali metal salt, which increases the concentration of the alkali metal salt, and improves the production efficiency.

According to the embodiments of the present disclosure, the method further includes: dispensing 60 wt % to 95 wt % of the evaporated solution containing the alkali metal taurinate to the at least one ion exchange resin column treated by the first activation manner, and dispensing 5 wt % to 40 wt % of the evaporated solution containing the alkali metal taurinate to the at least one ion exchange resin column treated by the second activation manner. According to the embodiments of the present disclosure, 5 wt %, 10 wt %, 15 wt %, 20 wt %, 25 wt %, 30 wt %, 35 wt % or 40 wt % of the evaporated solution is dispensed into the at least one ion exchange resin column treated by the second activation manner, and 60 wt %, 65 wt %, 70 wt %, 75 wt %, 80 wt %, 85 wt %, 90 wt % or 95 wt % of the evaporated solution is dispensed into the at least one ion exchange resin column treated by the first activation manner. Upon extensive studies, the inventors have found that in the production process of taurine with the system of the present disclosure, extra strong alkali is added in the ammonolysis reaction process to adjust a pH value of the reaction system, and a small part of the strong alkali for adjusting the pH value will consume some active groups in the resin in the ion exchange process. If an ion exchange resin column is activated with sulfurous acid, one metal ion is displaced with one sulfurous acid to form an alkali metal salt, and one alkali metal salt can correspondingly produce one taurine molecule. Thus, if an ion exchange resin column is activated with sulfurous acid that is produced by dissolving sulfur dioxide with alkali metal bisulfite, excessive alkali metal bisulfite will be present in the production system, a part of the alkali metal bisulfite cannot be recycled and reused, and excessive alkali metal ions are present in the production system. In order to solve this problem, a redundant alkali metal bisulfite solution needs to be disposed. However, the direct sewage disposal is high in cost and low in efficiency; and if an evaporation and concentration process is adopted, sodium bisulfite, sodium sulfite, etc. are unstable, and a salt obtained has high impurity content and cannot be sold, causing the waste of materials. By extensive studies and a large number of experimental designs, the inventors have found that if the ion exchange resin column activated by the first activation manner and the ion exchange resin column activated by the second activation manner are used to produce taurine from an evaporated solution at the same time, during activation of an exchange resin column with sulfuric acid, a part of alkali metal ions can be transformed into alkali metal sulfate that belongs to strong alkali salts, and the alkali metal sulfate can be directly concentrated by evaporation to form a pure product that can be sold or used. The disposal method is simple and saves cost and resources.

According to the embodiments of the present disclosure, a ratio of the evaporated solution dispensed to the at least one ion exchange resin column treated by the first activation manner to the evaporated solution dispensed to the at least one ion exchange resin column treated by the second activation manner ranges from (3:2) to (19:1).

According to the embodiments of the present disclosure, the method further includes, prior to activation: independently determining a concentration of alkali metal ions in an input solution of each of the at least one ion exchange resin column and a concentration of alkali metal ions in the ion exchange resin column to determine an activation manner of the activation to be performed on the ion exchange resin column, wherein the input solution and the output solution contain alkali metal taurinate ions.

According to the embodiments of the present disclosure, the method further includes: changing, in response to the concentration of alkali metal ions in the output solution of the ion exchange resin column that is being treated by the first activation manner being greater than or equal to 60% of the concentration of alkali metal ions in the input solution of the ion exchange resin column, the activation manner of the ion exchange resin column to the second activation manner, and changing, in response to the concentration of alkali metal ions in the output solution being smaller than or equal to 5% of the concentration of alkali metal ions in the input solution, the activation manner of the ion exchange resin column to the first activation manner. According to the embodiments of the present disclosure, when the concentration of alkali metal ions in the output solution is greater than or equal to 60% of the concentration of alkali metal ions in the input solution, it indicates that the ion exchange resin column is not in a good use condition, excessive alkali metal ions are present in the ion exchange resin column, ion exchange performed on alkali metal salt taurine is inefficient, the activation manner performed on the ion exchange resin column needs to be changed, and the ion exchange resin column needs to be activated with sulfuric acid. When the concentration of alkali metal ions in the output solution is smaller than or equal to 5% of the concentration of alkali metal ions in the input solution, it indicates that the ion exchange resin column is in a recovered state and can be further activated with sulfurous acid (an alkali metal bisulfite solution in which sulfur dioxide is dissolved), and activation with sulfurous acid will have a higher efficiency, which is beneficial to the efficient preparation of taurine in the continuous production process.

According to the embodiments of the present disclosure, a concentration of the alkali metal bisulfite ranges from 30 wt % to 40 wt %, preferably 35 wt %. According to the embodiments of the present disclosure, the concentration of the alkali metal bisulfite is 30 wt %, 31 wt %, 32 wt %, 33 wt %, 34 wt %, 35 wt %, 36 wt %, 37 wt %, 38 wt %, 39 wt %, or 40 wt %.

According to the embodiments of the present disclosure, the concentration of the alkali metal sulfate ranges from 2 wt % to 15 wt %, preferably from 5 wt % to 10 wt %. According to the embodiments of the present disclosure, the concentration of the alkali metal sulfate is 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, or 15 wt %.

BRIEF DESCRIPTION OF DRAWINGS

The above and/or additional aspects and advantages of the present disclosure will become apparent and readily understood from the following description of the embodiments in conjunction with the accompanying drawings, in which.

DESCRIPTION OF EMBODIMENTS

Figure 1:
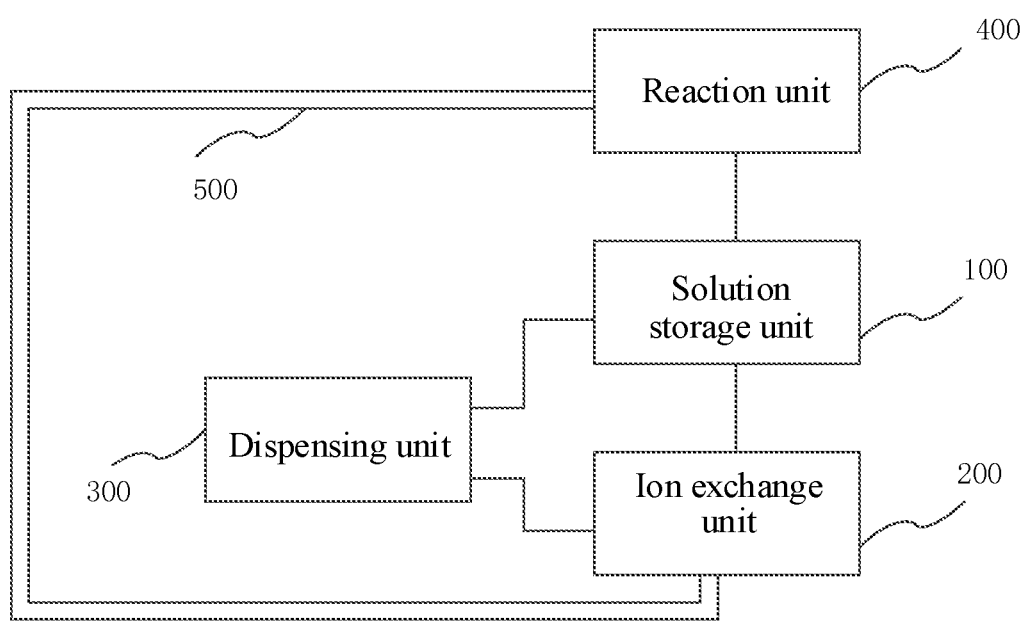
FIG. 1 is a schematic diagram of a system for preparing taurine according to embodiments of the present disclosure.

The embodiments of the present disclosure will be described below in detail, and examples of the embodiments are shown in the drawings. The embodiments described below with reference to the drawings are exemplary, and are intended to explain the present disclosure and should not be construed as limiting the present disclosure.

Explanation of Terms

Unless otherwise specified, the terms "first", "second", "third", etc. herein are used for convenience of description and distinguishing, do not imply or express a difference in order or importance therebetween, and do not indicate that the content defined by "first", "second", "third", etc. is composed of only one component.

In the present disclosure, unless otherwise expressly specified and limited, the terms "install", "link", "connect", "fix", etc. should be understood in a broad sense. For example, it may be a fixed connection, a detachable connection, or an integrated body; it may be a mechanical connection or an electrical connection; it may be a direct connection or an indirect connection through an intermediate; and it may be internal communication between two elements or interaction relationship between the two elements. Those of ordinary skill in the art can understand the specific meanings of the above terms in the present disclosure according to specific situations.

In the present disclosure, unless otherwise expressly specified and limited, a first feature being "above" or "below" a second feature may mean that the first feature is in direct contact with the second feature, or the first feature is in indirect contact with the second feature through an intermediate. Moreover, the first feature being "above", "over", or "on" the second feature may mean that the first feature is directly or obliquely above the second feature, or simply means that the first feature has a higher level than the second feature. The first feature being "below", "under" or "beneath" the second feature may mean that the first feature is just or obliquely below the second feature, or simply means that the first feature has a lower level than the second feature.

It should be noted that "alkali metal salt", "alkali metal", etc. herein include "sodium salt, potassium salt and/or lithium salt", "sodium, potassium and/or lithium". For example, alkali metal bisulfite refers to sodium bisulfite, potassium bisulfite or lithium bisulfite.

It should be noted that the alkali metal salt herein is preferably sodium salt.

It should be noted that an original evaporated solution herein refers to an evaporated solution obtained by evaporation or flash evaporation after an ammonolysis reaction. The evaporated solution has not been treated with any diluent, and has not been reacted with any other reagent (e.g., an acid solution).

It should be noted that the evaporated solution herein includes the original evaporated solution and/or an evaporated solution that has been subjected to treatment, and the treatment includes, but is not limited to, dilution with water or other solutions, neutralization with an acid solution (e.g., isethionic acid), etc.

It should be noted that a resin column, an ion exchange resin column, an ion exchange column, etc. herein all refer to a weakly acidic cation resin column having an acidity that is slightly higher than that of taurine.

In a first aspect, the present disclosure proposes a system for preparing taurine. Referring to FIG. 1, according to the embodiments of the present disclosure, the system includes: a solution storage unit 100 configured to store a solution containing alkali metal taurinate that is prepared by an ethylene oxide process; an ion exchange unit 200 connected to the solution storage unit 100 and including at least one ion exchange resin column; and a dispensing unit 300 connected to the solution storage unit 100 and the ion exchange unit 200 respectively, and configured to adjust an amount of the solution conveyed from the solution storage unit 100 to each of the at least one ion exchange resin column in the ion exchange unit 200. Each ion exchange resin column is activated independently by a first activation manner or a second activation manner, the first activation manner uses sulfurous acid for activation to obtain alkali metal bisulfite and taurine, and the second activation manner uses sulfuric acid for activation to obtain alkali metal sulfate and taurine. According to the embodiments of the present disclosure, the system has high efficiency, energy saving, and resource saving advantages.

According to the embodiments of the present disclosure, the system further includes: a reaction unit 400 connected to the solution storage unit 100 and configured to prepare an evaporated solution containing alkali metal taurinate by the ethylene oxide process; and an alkali metal bisulfite pipeline 500 connected to the ion exchange unit 200 and the reaction unit 400 respectively, and configured to return the alkali metal bisulfite to the reaction unit 400. Alkali metal bisulfite in an activating reagent and alkali metal bisulfite produced after activation can flow back to the reaction unit 400 via the alkali metal bisulfite pipeline 500 and undergo an addition reaction with ethylene oxide to produce alkali metal isethionate.

According to the embodiments of the present disclosure, the number of the ion exchange resin columns in the ion exchange unit is not limited, which may be one, two or more. At the same time, a quantity ratio of ion exchange resin columns treated by the first activation manner to ion exchange resin columns treated by the second activation manner may be 1:1, 2:1, or 3:1, preferably 1:1 or 2:1.

In a second aspect, the present disclosure proposes a method for preparing taurine. According to embodiments of the present disclosure, the method includes: preparing an evaporated solution containing alkali metal taurinate by an ethylene oxide process in a reaction unit; independently treating each of at least one ion exchange resin column in an ion exchange unit by a first activation manner or a second activation manner; dispensing a part of the evaporated solution containing the alkali metal taurinate to the at least one ion exchange resin column treated by the first activation manner to obtain alkali metal bisulfite and taurine, and inputting the alkali metal bisulfite into the reaction unit; and dispensing the other part of the evaporated solution containing the alkali metal taurinate to the at least one ion exchange resin column treated by the second activation manner to obtain alkali metal sulfate and taurine.

Figure 2:
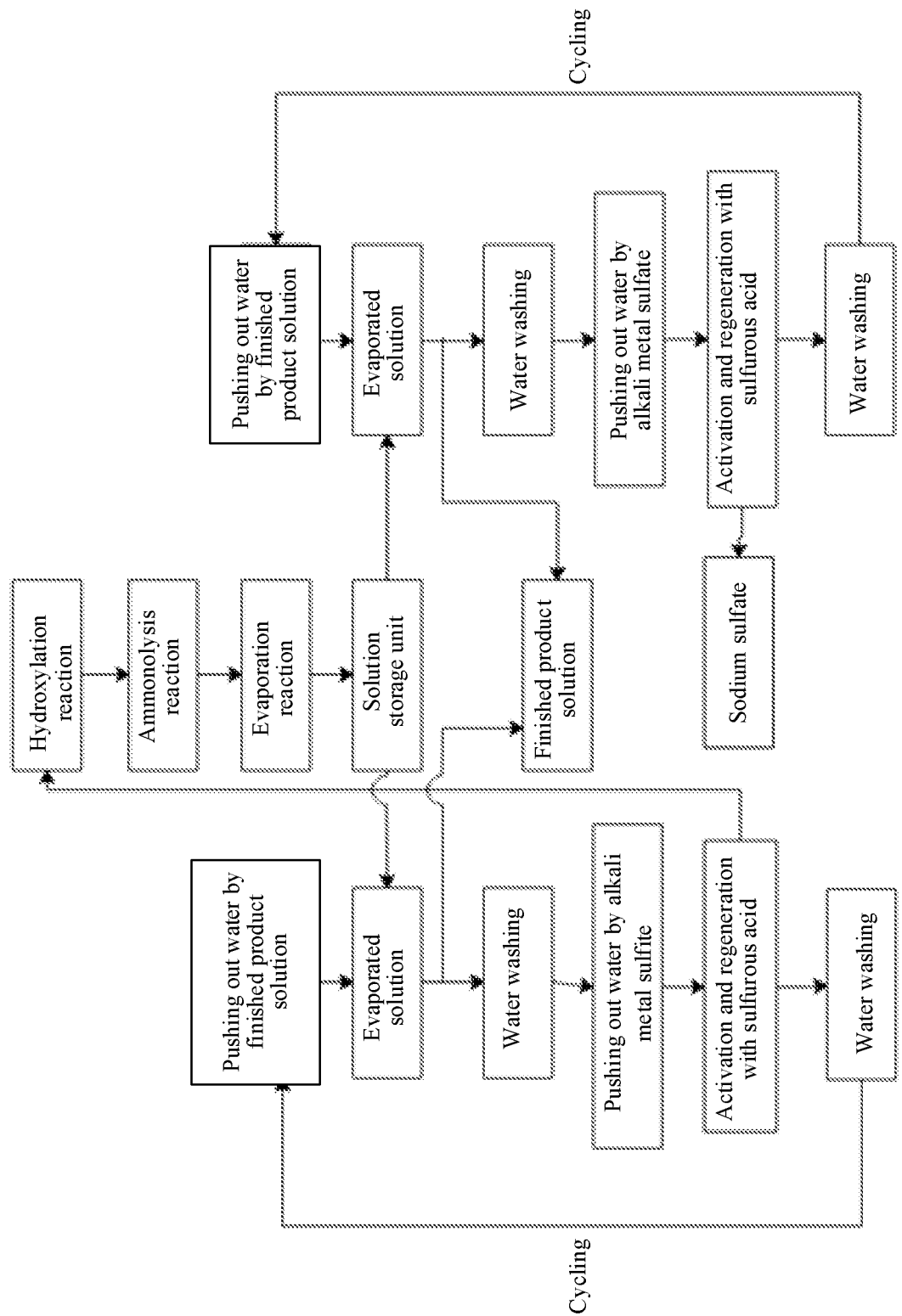
FIG. 2 is a flowchart of a method for preparing taurine according to embodiments of the present disclosure.

Referring to FIG. 2, according to a specific embodiment of the present disclosure, the method includes specific steps as follows.

1. Ethylene oxide reacts with alkali metal bisulfite to prepare alkali metal isethionate which reacts with ammonia under alkaline conditions to prepare alkali metal taurinate, and the solution obtained after ammonolysis reaction is subjected to flash evaporation and/or evaporation to remove redundant ammonia, so as to obtain the evaporated solution.

2. The evaporated solution is dispensed to the resin columns in the ion exchange unit according to a proportion, that is, 60 wt % to 95 wt % of the evaporated solution enters the resin columns treated by the first activation manner, and 5 wt % to 40 wt % of the evaporated solution enters the resin columns treated in the second activation solution.

3. Before the evaporated solution is subjected to ion exchange, the ion exchange resin columns are subjected to water washing, acid washing, alkali washing, activation, and water washing again. The water washing is performed to remove common impurities from an ion resin before the ion resin is loaded into the column, and requires that the resin is water-washed until the solution obtained from the water washing becomes colorless and no bubble is produced. The acid washing and alkali washing are performed to remove residual small molecule impurities in the resin. In the acid washing process, generally strong acid with a hydrogen ion [H]$^+$ concentration of 1 mol/L is used, and the volume of the strong acid is 2 to 3 times that of the resin. After the acid washing, the resin needs to be subjected to water washing until a pH value is 2 to 4 so as to remove an acid solution from the resin, and then the resin is subjected to alkali washing. In the alkali washing process, generally strong alkali with a hydroxide ion [OH]$^-$ concentration of 1 mol/L is used, and the volume of the strong alkali is 2 to 3 times that of the resin. After the alkali washing, the resin needs to be subjected to water washing again until a final pH value is 9 to 10. After being cleaned, the resin is activated with a strongly acidic solution with a hydrogen ion [H]$^+$ concentration of 1 mol/L and a volume of 2 to 4 times that of the resin. After being activated, the resin is subjected to water washing again until a pH value is less than 9. The solution obtained from the last water washing after the activation can be directly reused to prepare acid for the next activation of the resin.

4. The evaporated solution is inputted into the ion exchange column treated by the first activation manner from top to bottom. If a pH value of an output solution of the resin is less than 3, the output solution is used to dilute and neutralize an original evaporated solution; if the pH value of the output solution is 3 to 8, the output solution containing taurine is collected; and if the pH value of the output solution is greater than 8, the evaporated solution is no longer inputted. The concentration of alkali metal ions in the output solution obtained at this step is detected.

5. Purified water is flowed through the ion exchange column from top to bottom to wash the resin that has been used, and an output solution of the resin produced in the washing process is used to dilute the evaporated solution, until no taurine is detected in the output solution. At this time, a pH value of the output solution is 9.5 to 10.5. This step can reduce the usage amount of water and save water.

6. After the resin column treated by the first activation manner is washed, a sodium bisulfite solution at a low concentration is inputted into the ion exchange column from bottom to top to push out residual water in the resin column. A part of the residual water that is pushed out is used to dilute the original evaporated solution so as to avoid the waste of water, and the other part of the residual water is discharged for external collection and disposal to avoid the mixing of sodium bisulfite into the evaporated solution.

7. After water is removed from the ion exchange column treated by the first activation manner, the ion exchange column is activated with a mixture of sulfur dioxide, sodium bisulfite, and sulfurous acid from top to bottom, the addition of the activating reagent is stopped in response to the pH value of the output solution being 3 to 4, and the output solution is stored and used to prepare sodium bisulfite.

8. After the resin column is activated by the first activation manner, purified water is inputted into the ion exchange column from top to bottom until no acid radical anion is detected in the output solution of the resin. At this time, a pH value of the output solution is about 4, the purified water is no longer inputted, and the output solution is used to prepare sodium bisulfite. According to the embodiments of the present disclosure, this step can reduce the usage amount of water, save water, and control the production cost.

9. An appropriate volume of a solution containing alkali metal sulfite is used to push out water in apertures of the resin in the ion exchange column activated by the first activation manner from bottom to top. The output solution obtained at this step is treated by two steps: the output solution with a pH value greater than 3 is returned to the evaporated solution, and the output solution with a pH value less than 3 is directly collected as a finished product solution. In response to the volume of the output solution being the same as a volume of the input solution entering the resin, the inputting of the solution containing alkali metal sulfite is stopped, and a diluted evaporated solution is inputted. According to the embodiments of the present disclosure, the ion exchange resin column is pre-treated with taurine, which can provide an alkali metal bisulfite-containing environment for the resin column in advance, reduce damage of a strongly alkaline evaporated solution to the resin column, use active groups in the resin column to the largest extent, improve the activation efficiency, protect the resin column, and prolong the service life of the resin column.

10. The steps of washing the resin, activating the resin, washing the resin, and inputting the evaporated solution are cycled to achieve efficient continuous production of taurine. However, when an ion exchange resin column is activated with a sulfurous acid system, the cycle number is increased due to incomplete activation of the resin, so that the system is collapsed, and cycling cannot be continued. Therefore, when an ion exchange column is being treated by the first activation manner, the first activation manner of the ion exchange resin column is adjusted to the second activation manner, namely the sulfuric acid activation manner, in response to the concentration of alkali metal ions in the output solution being greater than 60% of the concentration of alkali metal ions in the evaporated solution inputted. In the cycling process, in response to the concentration of alkali metal ions in the output solution being less than 5% of the concentration of alkali metal ions in the input solution, the activation manner is adjusted to the sulfurous acid activation manner.

11. When treated by the second activation manner, an ion exchange resin is subjected to the same steps as those performed by the first activation manner except the step of activation of the ion exchange resin column and the treatment prior to the activation.

12. When the second activation manner is adopted to treat an ion exchange resin, the treatment (an alkali metal salt is used to push out water) prior to the activation includes: pushing out residual water in the resin from bottom to top with an alkali metal salt after the resin column is subjected to water washing. A part of a solution that is pushed out and contains no sulfate ions is inputted into the original evaporated solution to dilute the evaporated solution, and the other part of the solution that is pushed out and contains sulfate ions is directly inputted into a diluted acid storage tank and used to prepare an activating reagent.

Figure 3:
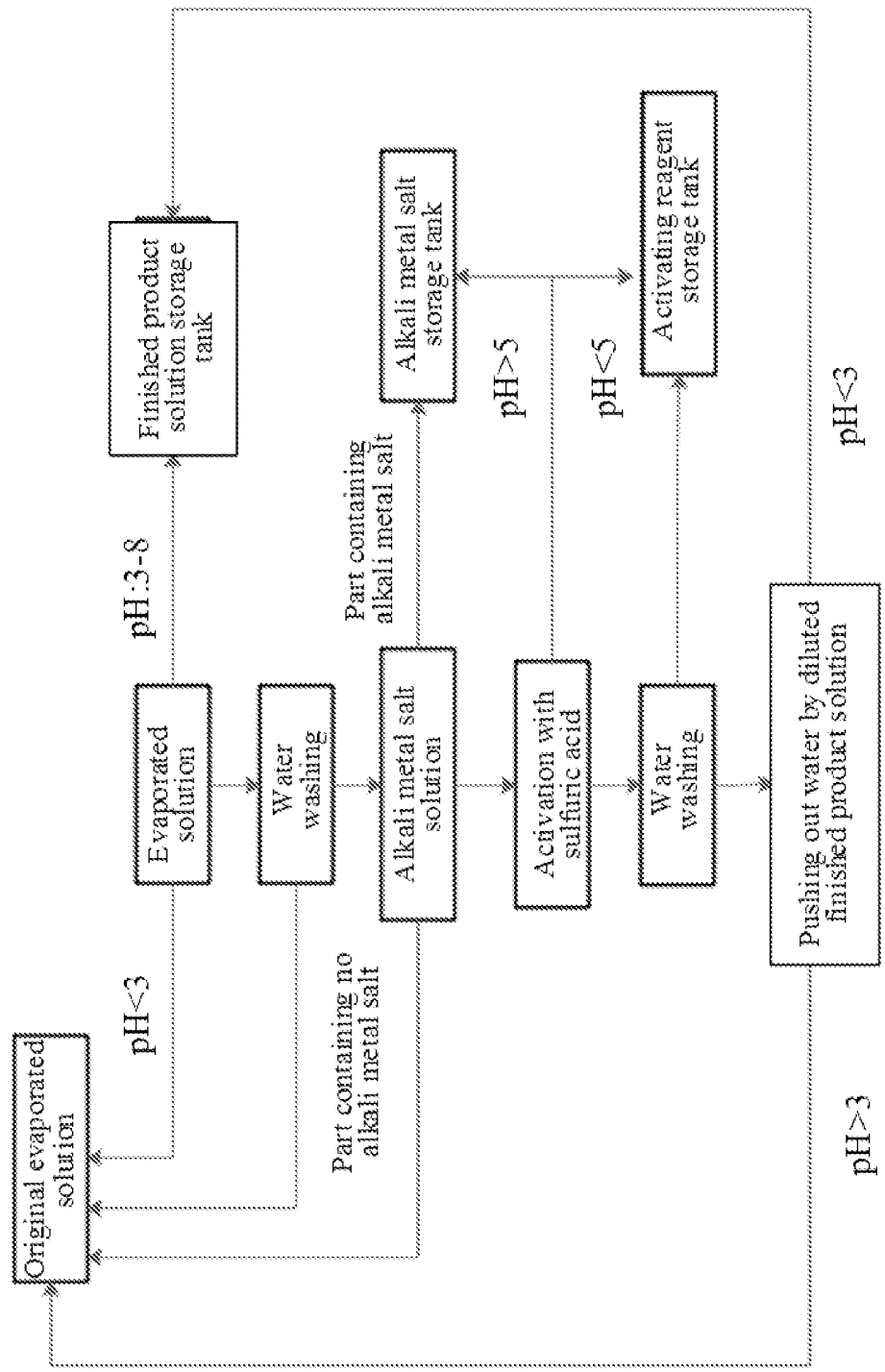
FIG. 3 is a flowchart of sulfuric acid activation according to embodiments of the present disclosure.

13. The second activation manner is performed with diluted sulfuric acid from top to bottom. The output solution with a pH value greater than 5 is inputted into a sodium sulfate storage tank, the output solution with a pH value less than 5 is inputted into the diluted acid storage tank, and the inputting of the dilute sulfuric acid is stopped in response the pH value of the output solution being less than 3. The activation process is shown in FIG. 3. In order to improve the activation efficiency, the concentration of the diluted sulfuric acid is less than 23% wt. By a large number of experiments, the inventors have found that after the evaporated solution is passed through the resin column, the resin column is subjected to water washing, and after the water washing, residual water in the resin column is pushed out with the output solution with a pH value from 5 to 5.5, and the output solution with a pH value less than 5 is used as a next batch activating reagent which contains a part of acid and a part of sodium sulfate. Increase of the concentration of sulfuric acid can reduce the use volume of sulfuric acid for activation to a small extent, but complete acid activation has little to do with the concentration of acid, and affects the subsequent step of purification of sodium sulfate. The saturated mass fraction of sodium sulfate is 31.6%, and at this time, a maximum concentration of the corresponding sulfuric acid is not greater than 23%. If the concentration of sulfuric acid is too high, sodium sulfate will be precipitated to cause solid blockage; a low concentration of the sulfuric acid has minimal damage to the resin, but a too low concentration in the production process can result in difficulties in subsequent purification of sodium sulfate, high usage amount of water, and thus a high cost.

The above order is not the specific order of the method for preparing taurine, and is only set herein for the convenience of understanding the present disclosure. In the actual production process, the number of ion exchange resin columns in the ion exchange unit and the activation manners can be adjusted according to the actual production capacity. That is, the first activation manner and the second activation manner can be performed alternately on the same ion exchange resin column, or performed on different ion exchange resin columns at the same time, or performed alternately on different ion exchange resin columns.

The present disclosure will be described below with reference to specific examples. It should be noted that these examples are only for the illustrative purpose, and are not construed as limiting the present disclosure.

Example 1

1. Resin pretreatment: 1 L of resin was loaded into a chromatographic column and pressed tightly, 3 to 5 cm of water was kept on the top of the resin, the resin was treated with a 4% sulfuric acid solution with a volume that is 3 times the volume of the resin at a flow rate of 2 to 4 times the volume of the resin per hour; after the treatment was completed, the resin was washed with tap water until a pH value of an output solution was greater than 4, then the resin was transformed with a 4% NaOH solution with a volume of 1.5-2 times the volume of resin (BV) at a flow rate of 2 to 4 times the volume of the resin per hour; after the transformation was completed, the resin was washed with tap water until a pH value of an output solution was less than 9. The resin was treated with a 4% sulfuric acid solution with a volume that is 3 times the volume of the resin at a flow rate of 2.5-5 BV/h, and after the treatment was completed, the resin was washed with tap water until a pH value of an output solution was greater than 4, so as to complete the activation of the resin for later use.

2. Flowing of evaporated solution sample through column: an original evaporated solution was diluted until the content of alkali metal taurinate was about 20 wt %, the diluted evaporated solution flowed through the column in a forward direction at a certain flow rate for adsorption, an end point was determined according to the requirements of different time periods, and various indicators were measured. After the flowing of the evaporated solution sample was completed, the ion exchange column was washed with water until a pH value of an output solution was 8 to 9, indicating that the elution was completed.

3. Regeneration of resin: the resin was treated by the first activation manner or the second activation manner.

4. Steps 2 and 3 were cycled in the same ion exchange column, and in each cycle, 100 L of the evaporated solution flowed through the column, and the cycle was repeated 10 times.

Allocated volume corresponding to activation at steps 3 and 4 are shown in Table 1.

TABLE 1

| | Allocated volume of taurine flowing through column for different activation manners | | | | | | | | | |
|---|---|---|---|---|---|---|---|---|---|---|
| | 1 | 2 | 3 | 4 | 5 | 6 | 7 | 8 | 9 | 10 |
| First activation manner | 100 L | 100 L | 95 L | 95 L | 80 L | 80 L | 60 L | 60 L | 55 L | 55 L |

TABLE 1-continued

Allocated volume of taurine flowing through column for different activation manners

| | 1 | 2 | 3 | 4 | 5 | 6 | 7 | 8 | 9 | 10 |
|---|---|---|---|---|---|---|---|---|---|---|
| Second activation manner | 0 | 0 | 5 L | 5 L | 20 L | 20 L | 40 L | 40 L | 45 L | 45 L |

Results are shown in Table 2.

TABLE 2

Total molar quantity of produced taurine and total molar quantity of produced sodium bisulfite in Example 1

| | Molar quantity of taurine/mol | | | |
|---|---|---|---|---|
| | First activation manner | Second activation manner | Total molar quantity of taurine/mol | Molar quantity of newly produced sodium bisulfite/mol |
| 1 | 15.2 | 0 | 15.2 | 16.9 |
| 2 | 15.3 | 0 | 15.3 | 16.8 |
| 3 | 14.6 | 0.79 | 15.19 | 15.7 |
| 4 | 14.4 | 0.78 | 15.18 | 15.6 |
| 5 | 12.3 | 3.0 | 15.1 | 14.6 |
| 6 | 12.1 | 3.1 | 15.2 | 14.5 |
| 7 | 9.1 | 6.2 | 15.3 | 12.1 |
| 8 | 9.2 | 6.21 | 15.33 | 12.7 |
| 9 | 8.3 | 7.1 | 15.4 | 9.8 |
| 10 | 8.2 | 7.5 | 15.1 | 10.0 |

It can be seen from Table 2 that, flowing and transformation of 100 L of evaporated solution at a (alkali metal taurinate) concentration of 20 wt % through one ion resin column produce taurine, 10 samples of 100 L of evaporation solutions were used for 10 cycles (100 L each cycle), and the activation manner performed on the resin is changed every two cycles. As shown in Table 1, for the first and second cycles, 100 L of evaporated solution flowed through the column and the adopted activation manner was the first activation manner and for the third to tenth cycles, activation by the first activation manner was used for a flowing volume of 95 L, 80 L, 60 L, and 55 L of evaporated solution, and activation by the second activation manner was used for the remaining flowing volume of 5 L, 20 L, 40 L, and 45 L of evaporated solution. It can be seen from Table 2 that when 100 L of evaporated solution flows through the column and the first activation manner was adopted, the molar quantity of produced sodium bisulfite is greater than the molar quantity of sodium taurinate entering the system. In the present disclosure, in the ethylene oxide process for preparing taurine, 1 mol of alkali metal sulfite correspondingly produces 1 mol of taurine. As for 100 L of evaporated solution, when activation by the first activation manner was used for a flowing volume of 95 L of evaporated solution, and activation by the second activation manner was used for a flowing volume of 5 L of evaporated solution, the content of the newly produced sodium bisulfite is still higher than that of the produced taurine (this is because in the cycling system, sodium bisulfite is used to push out water, a small amount of sodium is discharged and disposed as sewage, and the balance of sodium in the system can be basically achieved). As for 100 L of evaporated solution, when the first activation manner was used for a flowing volume of 80 L, 60 L or 55 L of evaporated solution, and the second activation manner was used for a flowing volume of 20 L, 40 L or 45 L of evaporated solution, the molar quantity of the newly produced sodium bisulfite is less than the total molar quantity of taurine, no redundant sodium bisulfite needs to be disposed in the system, and extra sodium bisulfite is needed to supplemented to produce taurine. However, supplement of excessive sodium bisulfite to the system is not beneficial to improvement of the overall production efficiency. Through comprehensive consideration, a total volume of the evaporated solution for the treatment with the first activation manner accounts for 60% to 95%, and a total volume of the evaporated solution for the treatment with the second activation manner accounts for 5% to 40%.

Example 2

Comparative Example 1

1. Resin pretreatment: 6 L of resin was loaded into a chromatographic column and pressed tightly, 3 to 5 cm of water was kept on the top of the resin, the resin was treated with a 4% sulfuric acid solution with a volume that is 3 times the volume of the resin at a flow rate of 2 to 4 times the volume of the resin per hour; after the treatment was completed, the resin was washed with tap water until a pH value of an output solution was greater than 4, then the resin was transformed with a 4% NaOH solution with a volume of 1.5 to 2 BV at a flow rate of 2 to 4 times the volume of the resin per hour, and after the transformation was completed, the resin was washed with tap water until a pH value of an output solution was less than 9. The resin was treated with a 4% sulfuric acid solution with a volume that is 3 times the volume of the resin at a flow rate of 2.5 to 5 BV/h, and after the treatment was completed, the resin was washed with tap water until a pH value of an output solution was greater than 4, so as to complete the activation of the resin for later use.

2. Loading of resin into column: 6 L of activated resin was loaded into two chromatographic columns equally and pressed tightly, 3-5 cm of water was kept on the top of each resin, and the resin columns were numbered as A1 and B1, respectively.

3. Flowing of evaporated solution sample through column: an original evaporated solution was diluted until the concentration of alkali metal taurinate was about 20 wt %, the diluted evaporated solution flowed through the column in a forward direction at a certain flow rate for adsorption, an end point was determined according to the requirements of different time periods, and various indicators were measured. After the flowing of the evaporated solution sample was completed, the resin column was washed with water until a pH value of an output solution was 8 to 9, indicating that elution was completed.

4. Regeneration of resin: the resin column A1 was treated by the first activation manner, and the resin column B1 was treated by the second activation manner.

Steps 3 and 4 were cycled, 100 L of evaporated solution flowed through the ion resin column A1, a total quantity of the finally obtained taurine was detected, and a content of the newly produced sodium bisulfite was also detected.

Comparative Example 2

3. Flowing of evaporated solution sample through columns: an original evaporated solution was diluted until the concentration of alkali metal taurinate was about 20 wt %, the diluted evaporated solution flowed through the column in a forward direction at a certain flow rate for adsorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: the resin column A1 was treated by the first activation manner, and the resin column B1 was treated by the second activation manner.

Steps 3 and 4 were cycled, 95 L of evaporated solution flowed through the ion resin column A1, 5 L of evaporated solution flowed through the ion resin column B2, the total quantity of the finally obtained taurine was detected, and the content of the newly produced sodium bisulfite was also detected.

Comparative Example 3

3. Flowing of evaporated solution sample through column: an original evaporated solution was diluted until the concentration of alkali metal taurinate was about 20 wt %, the diluted evaporated solution flowed through the column in a forward direction at a certain flow rate for adsorption, an end point was determined according to the requirements of different time periods, and various indicators were measured. After the flowing of the evaporated solution was completed, the resin column was washed with water until a pH value of an output solution was 8 to 9, indicating that elution was completed.

4. Regeneration of resin: the resin column A1 was treated by the first activation manner, and the resin column B1 was treated by the second activation manner.

Steps 3 and 4 were cycled, 80 L of evaporated solution flowed through the ion resin column A1, 20 L of evaporated solution flowed through the ion resin column B2, the total quantity of the finally obtained taurine was detected, and the content of the newly produced sodium bisulfite was also detected.

Comparative Example 4

3. Flowing of evaporated solution sample through column: an original evaporated solution was diluted until the concentration of alkali metal taurinate was about 20 wt %, the diluted evaporated solution flowed through the column in a forward direction at a certain flow rate for adsorption, an end point was determined according to the requirements of different time periods, and various indicators were measured. After the flowing of the evaporated solution was completed, the resin column was washed with water until a pH value of an output solution was 8 to 9, indicating that elution was completed.

4. Regeneration of resin: the resin column A1 was treated by the first activation manner, and the resin column B1 was treated by the second activation manner.

Steps 3 and 4 were cycled, 60 L of evaporated solution flowed through the ion resin column A1, 40 L of evaporated solution flowed through the ion resin column B2, the total quantity of the finally obtained taurine was detected, and the content of the newly produced sodium bisulfite was also detected.

Comparative Example 5

3. Flowing of evaporated solution sample through column: an original evaporated solution was diluted until the concentration of alkali metal taurinate was about 20 wt %, the diluted evaporated solution flowed through the column in a forward direction at a certain flow rate for adsorption, an end point was determined according to the requirements of different time periods, and various indicators were measured. After the flowing of the evaporated solution was completed, the resin column was washed with water until a pH value of an output solution was 8 to 9, indicating that elution was completed.

4. Regeneration of resin: the resin column A1 was treated by the first activation manner, and the resin column B1 was treated by the second activation manner.

Steps 3 and 4 were cycled, 55 L of evaporated solution flowed through the ion resin column A1, 45 L of evaporated solution flowed through the ion resin column B2, the total quantity of the finally obtained taurine was detected, and the content of the newly produced sodium bisulfite was also detected.

Results are shown in the following table.

TABLE 3

Total molar quantity of produced taurine and total molar quantity of produced sodium bisulfite in Comparative Examples 1 to 5 of Example 2

| | Molar quantity of taurine/mol | | Total molar quantity of taurine/mol | Molar quantity of newly produced sodium bisulfite/mol |
|---|---|---|---|---|
| | A1 | B1 | | |
| Comparative Example 1 | 15.2 | 0 | 15.2 | 16.8 |
| Comparative Example 2 | 14.4 | 0.78 | 15.18 | 15.7 |
| Comparative Example 3 | 12.1 | 3.1 | 15.2 | 14.5 |
| Comparative Example 4 | 9.1 | 6.2 | 15.3 | 12.1 |
| Comparative Example 5 | 8.3 | 7.1 | 15.4 | 9.8 |

It can be seen from Table 3 that flowing and transformation of 100 L of 20 wt % evaporated solution through the ion resin columns A1 and B1 obtain taurine. In Comparative Example 1, the evaporated solution all flowed through the column A1 (the resin was activated by the first activation manner), and the molar quantity of finally produced sodium bisulfite is greater than the molar quantity of sodium taurinate entering the system. In the present disclosure, in the ethylene oxide process for preparing taurine, 1 mol of alkali metal sulfite correspondingly produces 1 mol of taurine. In Comparative Example 2, 95 L of evaporated solution flowed through the column A1, 5 L of evaporated solution flowed through the column B1 (column B1 was treated by the second activation manner), and the content of newly produced sodium bisulfite was still higher than that of produced taurine (that is because in the cycling system, a small amount of sodium in a portion of sodium bisulfite used to push out water was discharged and disposed as sewage, and the balance of sodium in the system can be basically achieved). In Comparative Examples 3, 4 and 5, 80 L, 60 L, and 55 L of evaporated solutions flowed through the column A1, 20 L, 40 L, and 45 L of evaporated solutions flowed through the column B1, the molar quantity of newly produced sodium bisulfite is less than the total molar quantity of taurine, no redundant sodium bisulfite needs to be disposed in the system, and extra sodium bisulfite is needed to supplemented to produce taurine. However, supplement of excessive sodium bisulfite to the system is not beneficial to improvement of the overall production efficiency. Through comprehensive consideration, a total volume of the evaporated solution entering the ion exchange resin column that is treated by the first activation manner accounts for 60% to 95%, and a total volume of the evaporated solution entering the ion exchange resin column that is treated by the second activation manner accounts for 5% to 40%.

Example 3

1. Resin pretreatment: 6 L of resin was loaded into a chromatographic column and pressed tightly, 3 to 5 cm of water was kept on the top of the resin, the resin was treated with a 4% sulfuric acid solution with a volume that is 3 times the volume of the resin at a flow rate of 2 to 4 times the volume of the resin per hour; after the treatment was completed, the resin was washed with tap water until a pH value of an output solution was greater than 4, then the resin was transformed with a 4% NaOH solution with a volume of 1.5-2 BV at a flow rate of 2-4 times the volume of the resin per hour, and after the transformation was completed, the resin was washed with tap water until a pH value of an output solution was less than 9. The resin was treated with a 4% sulfuric acid solution with a volume that is 3 times the volume of the resin at a flow rate of 2.5-5 BV/h, and after the treatment was completed, the resin was washed with tap water until a pH value of an output solution was greater than 4, so as to complete the activation of the resin for later use.

2. Loading of resin into column: 6 L of activated resin was loaded into each of six chromatographic columns in an equal volume and pressed tightly, 3 to 5 cm of water was kept on the top of the resin, and the resin columns were numbered as A, B, C, D, E, and F, respectively.

Comparative Example 6

3. Flowing of evaporated solution sample through column: 6 samples of 1.5 L of 20 wt % evaporated solution (1.5 L each portion) were diluted to volume according to a certain ratio and flowed through the columns in a forward direction at a certain flow rate for absorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: the resin in columns A, B, and C was activated with sulfurous acid, and the resin in columns D, E, and F was activated with sulfuric acid.

Steps 3 and 4 were cycled 40 times.

Comparative Example 7

3. Flowing of evaporated solution sample through column: 6 samples of 1.5 L of 20 wt % evaporated solution (1.5 L each portion) were diluted to volume according to a certain ratio and flowed through the columns in a forward direction at a certain flow rate for absorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: the resin in columns D, E, and F was activated with the sulfurous acid activation system, and the resin in columns A, B, and C was activated with sulfuric acid.

Steps 3 and 4 were cycled 40 times.

Comparative Example 8

3. Flowing of evaporated solution sample through column: 6 samples of 1.5 L of 20 wt % evaporated solution (1.5 L each portion) were diluted to volume according to a certain ratio and flowed through the columns in a forward direction at a certain flow rate for absorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: the resin in columns A, B, C and D was activated with the sulfurous acid activation system, and the resin in columns E and F was activated with sulfuric acid.

Steps 3 and 4 were cycled 40 times.

Comparative Example 9

3. Flowing of evaporated solution sample through column: 6 samples of 1.5 L of 20 wt % evaporated solution (1.5 L each portion) were diluted to volume according to a certain ratio and flowed through the columns in a forward direction at a certain flow rate for absorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: the resin in columns C, D, E and F was activated by the first activation manner, and the resin in columns A and B was activated by the second activation manner.

Steps 3 and 4 were cycled 40 times.

Comparative Example 10

3. Flowing of evaporated solution sample through column: 6 samples of 1.5 L of 20 wt % evaporated solution (1.5 L each portion) were diluted to volume according to a certain ratio and flowed through the columns in a forward direction at a certain flow rate for absorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: the resin in columns A, B, E and F was activated by the first activation manner, and the resin in columns C and D was activated by the second activation manner.

Steps 3 and 4 were cycled 40 times.

Results are shown in Table 4 and Table 5.

TABLE 4

Variation of transformed quantity of alkali metal salt in the evaporated solutions in Comparative Examples 6 and 7

| Cycle number | | $10^{th}$ cycle | $20^{th}$ cycle | $30^{th}$ cycle | $40^{th}$ cycle |
|---|---|---|---|---|---|
| Comparative Example 6 | A | 95.6% | 95.2% | 92.7% | 90.4% |
| | B | 96.7% | 95.2% | 93.4% | 90.2% |
| | C | 95.8% | 94.9% | 93.1% | 90.0% |
| | D | 95.3% | 95.1% | 95.1% | 95% |
| | E | 96.9% | 94.9% | 95.6% | 95% |
| | F | 95.8% | 96.1% | 96.3% | 95% |
| Comparative Example 7 | A | 94.7% | 95.4% | 96.3% | 95.3% |
| | B | 95.9% | 96.7% | 94.9% | 95.6% |
| | C | 96.3% | 96.3% | 94.5% | 96.1% |
| | D | 95.9% | 93.8% | 92.9% | 90.5% |
| | E | 94.8% | 94.6% | 91.8% | 89.5% |
| | F | 93.9% | 93.2% | 92.9% | 88.7% |

It can be seen from Table 4 that in Comparative Example 6, the resin in columns A, B, and C was activated by the first activation manner, and after the long-term activation, the activation efficiency of the resin was reduced, and the transformation efficiency is reduced as the cycle number is increased; the resin in columns D, E, and F was activated by the second activation manner, and after the long-term activation, the activation efficiency of the resin did not change, and the transformation efficiency of the evaporated solution was stable. In Comparative Example 7, the resin columns A, B, and C was activated by the second activation manner instead of the first activation manner adopted in Comparative Example 6, the results show that the transformation efficiency of the resin columns A, B, and C was recovered; the resin in columns D, E, and F was treated by the first activation manner, and as the number of activations is increased, the activation efficiency of the resin was reduced and the transformation efficiency of the resin was reduced.

TABLE 5

Variation of transformed quantity of evaporated solution in Comparative Examples 8, 9 and 10

| Cycle number | | $10^{th}$ cycle | $20^{th}$ cycle | $30^{th}$ cycle | $40^{th}$ cycle |
|---|---|---|---|---|---|
| Comparative Example 8 | A | 95.6% | 94.7% | 93.5% | 91.5% |
| | B | 96.7% | 94.6% | 93.6% | 92.5% |
| | C | 94.8% | 94.9% | 94.1% | 92.8% |
| | D | 95.8% | 94.5% | 93.3% | 93.1% |
| | E | 95.6% | 94.8% | 95.5% | 94.9% |
| | F | 96.7% | 95.3% | 97.6% | 97.1% |
| Comparative Example 9 | A | 93.5% | 94.8% | 95.6% | 96.1% |
| | B | 93.8% | 94.6% | 94.9% | 96.7% |
| | C | 92.7% | 91.8% | 89.9% | 88.5% |
| | D | 93.4% | 92.1% | 89.5% | 87.3% |
| | E | 96.12% | 94.8% | 93.6% | 92.7% |
| | F | 93.8% | 94.6% | 93.9% | 92.7% |
| Comparative Example 10 | A | 95.8% | 94.8% | 93.9% | 92.9% |
| | B | 96.4% | 94.9% | 93.8% | 93.1% |
| | C | 93.5% | 94.8% | 95.6% | 96.1% |
| | D | 93.8% | 94.6% | 94.9% | 96.7% |
| | E | 92.1% | 92.0% | 88.9% | 88.6% |
| | F | 93.1% | 91.8% | 89.7% | 87.5% |

It can be seen from the results shown in Table 5 that in Comparative Example 8, the resin columns A, B, C, and D were treated by the first activation manner, and the activation efficiency was reduced as the cycle number was increased. In Comparative Example 9, the resin columns A and B were treated by the second activation manner instead, the resin columns C and D were still treated by the first activation manner, and the activation efficiency of the resin columns C and D was further reduced. In Comparative Example 10, the resin columns C and D were treated by the second activation manner instead, and the transformation capacity of the resin was recovered to a high level.

Therefore, it can be seen from Comparative Examples 6 to 10 that for an ion exchange resin column treated by the first activation manner, if the resin is activated with sulfurous acid and sodium bisulfite for a long time, the transformation efficiency of the resin is reduced as the cycle number is increased, and after the resin is changed to be treated by the second activation manner, the transformation efficiency of the resin is recovered. It can be seen from the examples that for a resin column treated by the first activation manner, when the detected concentration of alkali metal in an output solution of the resin is about 60% of the concentration of alkali metal in the evaporated solution entering the resin column, it indicates that the activation manner needs to be changed to the second activation manner. For a resin column treated by the second activation manner, when the detected concentration of alkali metal in an output solution of the resin is about 5% of the concentration of alkali metal in the evaporated solution entering the resin column, it is determined that the resin column is completely activated, and can be treated by the first activation manner or the second activation manner.

Example 4

The resin column C or D of Comparative Example 10 was selected to undergo the following experiment, and the resin column was treated by the second activation manner.

3. Flowing of evaporated solution sample through column: an evaporated solution was diluted to a volume according to a certain ratio, a certain volume of pre-treated resin was transferred into a chromatographic column, the diluted evaporated solution flowed through the resin column in a forward direction at a certain flow rate for adsorption, an end point was determined according to the requirements of different time periods, and various indicators were measured. After the flowing of the evaporated solution was completed, the resin column was washed with water until a pH value of an output solution was 8 to 9, indicating that elution was completed.

4. Regeneration of resin: a sulfuric acid solution flowed through the column in a forward direction at a certain flow rate for desorption, it was determined that the resin was completely activated in response to detecting no sodium ion in an eluent, and then the resin column was washed with water until a pH value of an output solution was greater than 4.

Experimental steps 3 and 4 were repeated, the conditions of step 3 were kept unchanged, and the metal ion content in the activating reagent content of step 4 was changed. The conditions are shown in Table 6.

TABLE 6

Activation time under mixed eluents with the same sulfuric acid content (15 wt %) and different alkali metal ion contents

| | Batch number | | | | | | |
|---|---|---|---|---|---|---|---|
| Ingredient | 1 | 2 | 3 | 4 | 5 | 6 | 7 |
| Sulfuric acid | 15 wt % | 15 wt % | 15 wt % | 15 wt % | 15 wt % | 15 wt % | 15 wt % |
| Sodium ion salt | 0 | 2 wt % | 5 wt % | 8 wt % | 10 wt % | 12 wt % | 15 wt % |
| Activation time/min | 60 | 55 | 46 | 43 | 45 | 47 | 46 |

| | Batch number | | | | | | |
|---|---|---|---|---|---|---|---|
| Ingredient | 8 | 9 | 10 | 11 | 12 | 13 | 14 |
| Sulfuric acid | 15 wt % | 15 wt % | 15 wt % | 15 wt % | 15 wt % | 15 wt % | 15 wt % |
| Magnesium ion salt | 0 | 2 wt % | 5 wt % | 8 wt % | 10 wt % | 12 wt % | 15 wt % |
| Activation time | 61 | 57 | 49 | 48 | 48 | 50 | 51 |

TABLE 6-continued

Activation time under mixed eluents with the same sulfuric acid content (15 wt %) and different alkali metal ion contents

| Ingredient | Batch number | | | | | | |
|---|---|---|---|---|---|---|---|
| | 15 | 16 | 17 | 18 | 19 | 20 | 21 |
| Sulfuric acid | 15 wt % | 15 wt % | 15 wt % | 15 wt % | 15 wt % | 15 wt % | 15 wt % |
| Potassium ion salt | 0 | 2 wt % | 5 wt % | 8 wt % | 10 wt % | 12 wt % | 15 wt % |
| Activation time | 60 | 56 | 47 | 45 | 45 | 47 | 48 |

The results in Table 6 show that under the conditions of the same flow rate and the same sulfuric acid content, when the sodium salt content is zero, the resin needs to be activated for 60 min. The activation time of the resin is gradually reduced as the sodium ion salt content is increased. However, when the sodium ion salt content is increased to 10 wt % or more, the activation time does not change significantly, and in this case, a sodium salt is precipitated in the resin to block the column. Therefore, the optimal sodium ion salt content is between 5 wt % and 10 wt %. An enhancement effect of potassium ions is relatively consistent with that of sodium ions. An enhancement effect of a magnesium ion salt is relatively poor compared with that of a sodium ion salt, but still has an enhancement effect. Sodium ions and potassium ions are all metal ions of group I and have similar structures, and the main ions to be exchanged in the ion resin system are sodium ions, so the sodium salt and the potassium salt show a strong enhancement effect, and increase of the metal ion salts in the activating reagent can improve the activation efficiency and shorten the activation time. If the same type of metal ion salt is increased for production, the concentration of the metal ion salt can be greatly increased, the evaporation cost is reduced, the subsequent recycling and reusing of the metal ion salt is enhanced, and the production cost is greatly saved.

Example 5

A variation curve of the solubility of sodium sulfate is as follows:

TABLE 7

Variation of solubility of sodium sulfate with temperature

| Temperature/° C. | 0 | 10 | 20 | 30 | 50 | 60 | 70 | 80 | 90 | 100 |
|---|---|---|---|---|---|---|---|---|---|---|
| Solubility | 4.9 | 9.1 | 19.5 | 40.8 | 46.2 | 45.3 | 44.3 | 43.7 | 42.7 | 42.5 |
| Saturated mass fraction g/g | 4.7% | 8.3% | 16.3% | 29% | 31.6% | 31.2% | 30.7% | 30% | 29.9% | 29.8% |

Figure 4:
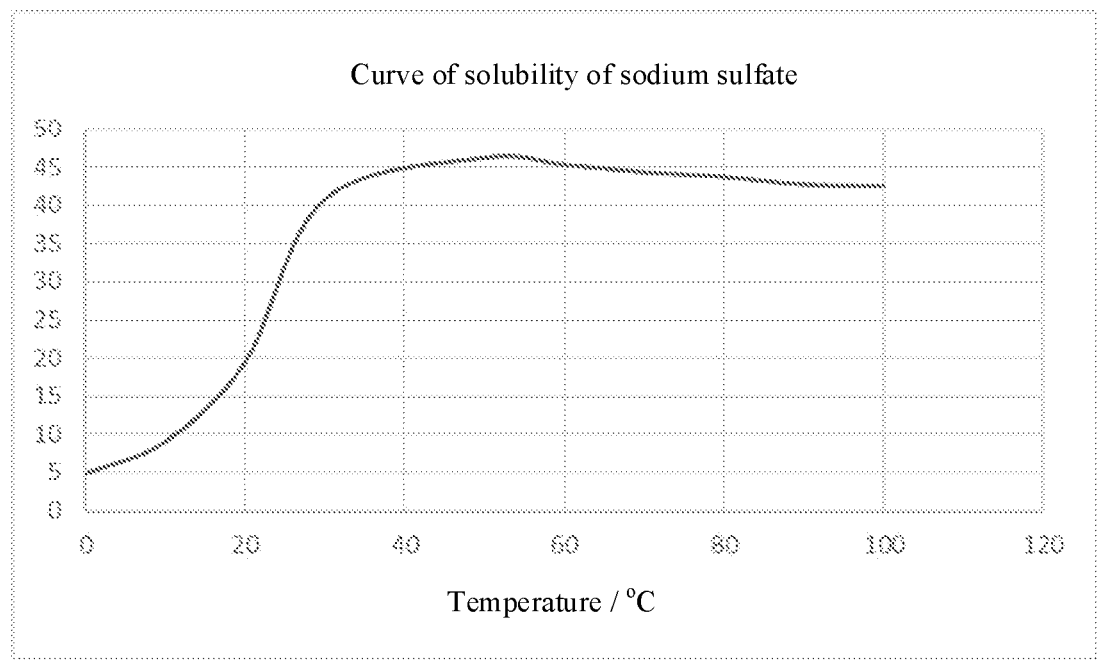
FIG. 4 is a variation curve of sodium sulfate with temperature according to embodiments of the present disclosure.

It can be seen from FIG. 4 that when the temperature is below 50° C., the solubility of sodium sulfate increases as the temperature increases, and when the temperature is above 50° C., the solubility of sodium sulfate slowly decreases as the temperature increases. It can be seen that when the temperature of the production system is kept at about 50° C., the acid concentration can be increased to the largest extent, and the content of sodium sulfate obtained at this temperature is the highest, which is beneficial to reduction of the cost of the subsequent concentration evaporation.

TABLE 8

Content of obtained sodium sulfate corresponding to content of sulfuric acid for acid activation

| Temperature/° C. | 0 | 10 | 20 | 30 | 50 | 60 | 70 | 80 | 90 | 100 |
|---|---|---|---|---|---|---|---|---|---|---|
| Solubility | 4.9 | 9.1 | 19.5 | 40.8 | 46.2 | 45.3 | 44.3 | 43.7 | 42.7 | 42.5 |
| Saturated mass fraction g/g | 4.7% | 8.3% | 16.3% | 29% | 31.6% | 31.2% | 30.7% | 30% | 29.9% | 29.8% |

It can be seen from Table 8 that when the content of sulfuric acid is 30%, the content of correspondingly produced sodium sulfate is 42.7%, and when the temperature of the ion resin in the production process is controlled at about 65° C., the saturated mass fraction of sodium sulfate is 44.3% to 44.5%. Considering a fact that when a resin is activated with sulfuric acid, the process of replacing sodium ions with $H^+$ ions will be shortly suspended, causing a short-term increase of the concentration of sodium sulfate in the activation process, and a possibility that sodium sulfate is precipitated to block the column, therefore, in the experiment, the content of sulfuric acid is adjusted to 15% to 25%. However, it is found from subsequent experiments that when the concentration reaches 25%, sodium sulfate will be also precipitated if the temperature is not well controlled, so the optimal sulfuric acid content is about 22%.

Based on the above analysis results, the resin column C or D of Comparative Example 10 was selected to undergo the following experiment.

3. Flowing of evaporated solution sample through column: an evaporated solution was diluted to a volume according to a certain ratio, a certain volume of pre-treated resin was transferred into a chromatographic column, the diluted evaporated solution flowed through the resin column in a forward direction at a certain flow rate for adsorption, an end point was determined according to the requirements of different time periods, and various indicators were measured. After the flowing of the evaporated solution was completed, the resin column was washed with water until a pH value of an output solution was 8 to 9, indicating elution was completed.

4. Regeneration of resin: a sulfuric acid solution flowed through the column in a forward direction at a certain flow rate for desorption, it was determined that the resin was completely activated in response to detecting no sodium ion in the eluent, and then the resin column was washed with water until a pH value of an output solution was greater than 4.

Experimental steps 3 and 4 were repeated, during which the conditions of step 3 were kept unchanged, and the content of the activating reagent of step 4 was changed. The conditions are shown in Table 9.

TABLE 9

Various parameters of complete activation of resin by acidic activating reagent at different contents

| Batch number | Sulfuric acid content | Usage volume of acid | Volume of water for washing after acid activation |
|---|---|---|---|
| 1 | 4.7 wt % | 22 L | 6.5 L |
| 2 | 9.8 wt % | 20 L | 7 L |
| 3 | 12 wt % | 17 L | 7.3 L |
| 4 | 15 wt % | 17 L | 7.5 L |
| 5 | 23 wt % | 15 L | 7.0 L |
| 6 | 25 wt % | 14 L | 6.9 L |

As shown in Table 9, under the same conditions, the total usage volume of acid for activation is reduced as the acid content is increased. In conjunction with the control analysis of sulfuric acid content, the current data shows that the activation of the resin is relatively stable under the sulfuric acid content of 23 wt %. After the acid activation, the usage volume of water for washing is first increased and then reduced as the acid content is increased. As the acid content is increased subsequently, the usage volume of acid is reduced, and the resin can be easily washed to pH 4 to 6. However, in the experiment, when the content is as high as 25 wt %, a small amount of solid will be precipitated in the resin column if the temperature fluctuates, affecting the experiment. Therefore, taking the actual conditions into consideration, the sulfuric acid content is preferably 23 wt %.

Herein, description with reference to the terms "an embodiment", "some embodiments", "example", "specific example" or "some examples", etc. refers to that specific features, structures, materials or characteristics described in conjunction with the embodiment or example are included in at least one embodiment or example of the present disclosure. Herein, schematic representations of the above terms are not necessarily directed to the same embodiment or example. Furthermore, the specific features, structures, materials or characteristics described may be combined in any suitable manner in any one or more embodiments or examples. In addition, those skilled in the art may combine and integrate different embodiments or examples described herein, as well as features of different embodiments or examples, without conflicting each other.

While the embodiments of the present disclosure have been illustrated and described above, it should be understood that the above embodiments are exemplary and are not construed as limiting the present disclosure. Those of ordinary skill in the art can make change, modification, replacement, and variation to the above embodiments within the scope of the present disclosure.

What is claimed is:

1. A system for preparing taurine, comprising:
a solution storage unit configured to store a solution containing alkali metal taurinate, the solution being prepared by an ethylene oxide process;
an ion exchange unit comprising plurality of ion exchange resin columns each configured to be activated independently by a first activation manner or a second activation manner, the first activation manner using sulfurous acid for activation, and the second activation manner using sulfuric acid for activation, wherein each of the plurality of ion exchange resin columns is a weakly acidic cation resin column having an acidity higher than that of taurine; and
a dispensing unit connected to the solution storage unit and the ion exchange unit, the dispensing unit being configured to adjust an amount of the solution conveyed from the solution storage unit to each of the plurality of ion exchange resin columns in the ion exchange unit, and the dispensing unit being further configured to: dispense a part of the solution containing the alkali metal taurinate to at least one of the plurality of ion exchange resin columns treated by the first activation manner to obtain alkali metal bisulfite and taurine; and dispense the other part of the solution containing the alkali metal taurinate to at least one of the plurality of ion exchange resin columns treated by the second activation manner to obtain alkali metal sulfate and taurine.

2. The system according to claim 1, further comprising an activating solution change unit connected to each of the plurality of ion exchange resin columns and configured to change an activating solution for activating the plurality of ion exchange resin columns, and change an activation manner of the at least one of the plurality of ion exchange resin columns from the first activation manner to the second activation manner or from the second activation manner to the first activation manner.

3. The system according to claim 2, further comprising an alkali metal ion concentration detection module connected to an inlet and an outlet of each of the plurality of ion exchange resin columns, wherein the alkali metal ion concentration detection module is adapted to independently detect a concentration of alkali metal ions in an input solution of each of the plurality of ion exchange resin columns and a concentration of alkali metal ions in an output solution of each of the plurality of ion exchange resin columns, wherein both the input solution and the output solution contain alkali metal taurinate, and wherein the alkali metal ion concentration detection module is connected to the activating solution change unit to allow the activating solution change unit to change the activation manner of the at least one of the plurality of ion exchange resin columns from the first activation manner to the second activation manner or from the second activation manner to the first activation manner based on a detection result of the alkali metal ion concentration detection module.

4. The system according to claim 1, wherein the dispensing unit is configured to adjust an amount of the solution conveyed from the solution storage unit to each of the plurality of ion exchange resin columns independently,
an amount of the solution inputted into the at least one of the plurality of ion exchange resin columns treated by the first activation manner is 60 wt % to 95 wt % of a total amount of the solution in the solution storage unit, and an amount of the solution inputted into the at least one of the plurality of ion exchange resin columns treated by the second activation manner is 5 wt % to 40 wt % of the total amount of the solution in the solution storage unit;

optionally, a ratio of the amount of the solution inputted into the at least one of the plurality of ion exchange resin columns treated by the first activation manner to the amount of the solution inputted into the at least one of the plurality of ion exchange resin columns treated by the second activation manner ranges from (3:2) to (19:1).

5. The system according to claim 3, wherein the activating solution change unit is configured to:

change, in response to the concentration of alkali metal ions in the output solution of the at least one of the plurality of ion exchange resin columns that is being treated by the first activation manner being greater than 60% of the concentration of alkali metal ions in the input solution of the at least one of the plurality of ion exchange resin columns, the activation manner of the at least one of the plurality of ion exchange resin columns to the second activation manner, and change, in response to the concentration of alkali metal ions in the output solution being smaller than or equal to 5% of the concentration of alkali metal ions in the input solution, the activation manner of the at least one of the plurality of ion exchange resin columns to the first activation manner.

6. The system according to claim 5, further comprising a solution allocation module connected to a bottom of each of the plurality of ion exchange resin columns, wherein the solution allocation module is configured to:
input an alkali metal bisulfite solution into the at least one of the plurality of ion exchange resin columns from bottom to top before the at least one of the plurality of ion exchange resin columns is treated by the first activation manner; and input an alkali metal sulfate solution into the at least one of the plurality of ion exchange resin columns from bottom to top before the at least one of the plurality of ion exchange resin columns is treated by the second activation manner.

7. The system according to claim 5, wherein the second activation manner is adapted for a second activation treatment using sulfuric acid at a concentration smaller than or equal to 25 wt %.

8. The system according to claim 7, wherein the second activation manner is adapted for a second activation treatment using sulfuric acid at a concentration smaller than or equal to 23 wt %.

9. The system according to claim 5, wherein the sulfurous acid used by the first activation manner is obtained by dissolving sulfur dioxide in an alkali metal bisulfite solution, the alkali metal bisulfite solution having a concentration from 25 wt % to 50 wt %.

10. The system according to claim 1, further comprising:
a reaction unit connected to the solution storage unit and configured to prepare an evaporated solution containing the alkali metal taurinate by the ethylene oxide process; and an alkali metal bisulfite pipeline connected to the ion exchange unit and the reaction unit respectively, and configured to return the alkali metal bisulfite to the reaction unit.

11. A method for preparing taurine, comprising:
preparing an evaporated solution containing alkali metal taurinate by an ethylene oxide process in a reaction unit;

independently treating each of a plurality of ion exchange resin columns in an ion exchange unit by a first activation manner or a second activation manner;

dispensing a part of the evaporated solution containing the alkali metal taurinate to the at least one of the plurality of ion exchange resin columns treated by the first activation manner to obtain alkali metal bisulfite and taurine, and inputting the alkali metal bisulfite into the reaction unit; and dispensing the other part of the evaporated solution containing the alkali metal taurinate to at least one of the plurality of ion exchange resin columns treated by the second activation manner to obtain alkali metal sulfate and taurine.

12. The method according to claim 11, wherein the first activation manner further comprises:

passing alkali metal bisulfite through the at least one of the plurality of ion exchange resin columns from bottom to top;

dissolving sulfur dioxide in an alkali metal bisulfite solution to obtain a sulfurous acid solution; and passing the sulfurous acid solution through the at least one of the plurality of ion exchange resin columns from top to bottom to treat the at least one of the plurality of ion exchange resin columns by the first activation manner.

13. The method according to claim 11, wherein the second activation manner further comprises:

passing an alkali metal sulfate solution through the at least one of the plurality of ion exchange resin columns from bottom to top; and passing a sulfuric acid solution having a concentration smaller than or equal to 25 wt % through the at least one of the plurality of ion exchange resin columns from top to bottom to treat the at least one of the plurality of ion exchange resin columns by the second activation manner.

14. The method according to claim 11, further comprising: dispensing 60 wt % to 95 wt % of the evaporated solution containing the alkali metal taurinate to the at least one of the plurality of ion exchange resin columns treated by the first activation manner; and dispensing 5 wt % to 40 wt % of the evaporated solution containing the alkali metal taurinate to the at least one of the plurality of ion exchange resin columns treated by the second activation manner, optionally, a ratio of the evaporated solution dispensed to the at least one of the plurality of ion exchange resin columns treated by the first activation manner to the evaporated solution dispensed to the at least one of the plurality of ion exchange resin columns treated by the second activation manner ranges from (3:2) to (19:1).

15. The method according to claim 14, comprising, prior to activation:

independently determining a concentration of alkali metal ions in an input solution of each of the plurality of ion exchange resin columns and a concentration of alkali metal ions in the at least one of the plurality of ion exchange resin columns to determine an activation manner of the activation to be performed on the at least one of the plurality of ion exchange resin columns, wherein the input solution and an output solution contain alkali metal taurinate ions.

16. The method according to claim 15, comprising:
changing, in response to the concentration of alkali metal ions in the output solution of the at least one of the plurality of ion exchange resin columns that is being treated by the first activation manner being greater than or equal to 60% of the concentration of alkali metal ions in the input solution of the at least one of the plurality of ion exchange resin columns, the activation manner of the at least one of the plurality of ion exchange resin columns to the second activation manner, and changing, in response to the concentration of alkali metal ions in the output solution being smaller than or equal to 5% of the concentration of alkali metal ions in the input solution, the activation manner of the at least one of the plurality of ion exchange resin columns to the first activation manner.

17. The method according to claim 11, wherein a concentration of the alkali metal bisulfite ranges from 30 wt % to 40 wt %.

18. The method according to claim 17, wherein the concentration of the alkali metal bisulfite is 35 wt %.

19. The method according to claim 13, wherein a concentration of the alkali metal sulfate ranges from 2 wt % to 15 wt %.

20. The method according to claim 19, wherein the concentration of the alkali metal sulfate ranges from 5 wt % to 10 wt %.

* * * * *